United States Patent
Weyl et al.

(10) Patent No.: US 6,812,710 B2
(45) Date of Patent: Nov. 2, 2004

(54) GAS PROBE

(75) Inventors: Helmut Weyl, Schwieberdingen (DE); Juergen Wilde, Fellbach (DE)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 10/048,533

(22) PCT Filed: May 8, 2001

(86) PCT No.: PCT/DE01/01734
§ 371 (c)(1),
(2), (4) Date: Apr. 15, 2002

(87) PCT Pub. No.: WO01/96850
PCT Pub. Date: Dec. 20, 2001

(65) Prior Publication Data
US 2002/0148280 A1 Oct. 17, 2002

(30) Foreign Application Priority Data
Jun. 10, 2000 (DE) .......................................... 100 28 909

(51) Int. Cl.$^7$ ............................. G01N 27/62; G01N 7/00
(52) U.S. Cl. ...................................... 324/464; 73/31.05
(58) Field of Search ......................... 324/464; 73/31.05, 73/23.31; 204/426

(56) References Cited

U.S. PATENT DOCUMENTS

| | | | |
|---|---|---|---|
| 4,818,363 A | * | 4/1989 | Bayha et al. ............... 204/426 |
| 4,983,271 A | | 1/1991 | Kato et al. |
| 6,082,175 A | * | 7/2000 | Yoshikawa et al. ........ 73/23.31 |

FOREIGN PATENT DOCUMENTS

| | | |
|---|---|---|
| DE | 197 40 363 A | 3/1999 |
| EP | 0 087 626 A | 9/1983 |
| EP | 0 836 094 A | 4/1998 |

OTHER PUBLICATIONS

Patent Abstract of Japan, vol. 008, No. 031, (P–253), Feb. 9, 1984 & JP 58 184538 A (Nippon Tokushu Togyo KK), Oct. 28, 1983 Zusammenfassung: Abbildungen 6–10.

* cited by examiner

Primary Examiner—Jay Patidar
Assistant Examiner—Amy He
(74) Attorney, Agent, or Firm—Ronald E. Greigg

(57) ABSTRACT

The invention relates to a gas probe for installation in a measurement gas chamber, having a metal housing in which a planar sensor element is disposed, electrically insulated, with at least one contact face that is conductively connected to a metal conductor element. For the conductor element, an electrically insulating contact holder is provided, which presses the conductor element onto the contact face by a spring element that engages the contact holder. The conductor element is disposed in an indentation of the contact holder, which indentation is oriented toward the contact face of the sensor element, and by way of a region protruding out of the indentation of the contact holder, the conductor element is in contact with the contact face.

11 Claims, 2 Drawing Sheets

GAS PROBE

CROSS-REFERENCE TO RELATED APPLICATIONS

This is a 35 U.S.C. 371 application of PCT/DE 01/01734, filed on May 8, 2001.

BACKGROUND OF THE INVENTION

1. Field of the Invention

The invention is based on a gas probe for determining the concentration or temperature of a gas such as the exhaust gas components of an internal combustion engine.

2. Description of the Prior Art

One gas probe of the type with which this invention is concerned is known, for instance from European Patent Disclosure EP 0506897 B1, for use in exhaust gas analysis for internal combustion engines. Such gas probes have a metal housing, in which an elongated, planar sensor element is disposed, electrically insulated, with one region on the measurement side and one region on the connection side. In the connection region, the sensor element has contact faces, which are electrically connected to a measurement point located in the measurement region. The gas probe also has a contacting device, which contains conductor elements that are in conductive contact with the contact faces of the sensor element and which extend out of the housing. By means of a spring element that engages contact holder, the conductor elements are pressed onto the contact faces. The regions of the contact holder that contact the conductor elements are embodied in flat form.

One such gas probe is known, for instance from European Patent Disclosure EP 0506897 B1, for use in exhaust gas analysis for internal combustion engines. Such gas probes have a metal housing, in which an elongated, planar sensor element is disposed, electrically insulated, with one region on the measurement side and one region on the connection side. In the connection region, the sensor element has contact faces, which are electrically connected to a measurement point located in the measurement region. The gas probe also has a contacting device, which contains conductor elements that are in conductive contact with the contact faces of the sensor element and which extend out of the housing. By means of a spring element that engages a contact holder, the conductor elements are pressed onto the contact faces. The regions of the contact holder that contact the conductor elements are embodied in flat form.

Such gas probes serve to measure the temperature or determine the concentration of gas components in exhaust gases of internal combustion engines. To that end, the gas probe is secured in a measurement opening of an exhaust gas line of an internal combustion engine. The exhaust gas can reach temperatures of more than 1000° C. in the exhaust gas line, and thus the gas probe is severely heated, and temperatures up to 800° C. occur in the region of the contacting device. At such high temperatures, the conductor elements can become deformed by creeping processes. As a result, the deflection of the spring element out of its position of repose and thus the contact pressure can be decreased, and the contact of the conductor elements with the contact faces can be impaired or even disrupted entirely.

From European Patent Disclosure EP 0 087 626 B1, a gas probe with a clamp contact means is also known, with which means conductor elements bent into a U shape are put into contact, by means of a contact holder, with contact faces of a planar sensor element. The contact holder has a slot for receiving the sensor element. Through holes are also made in the contact holder, as well as indentations laterally on the slot. The indentations serve to receive one leg of the conductor element bent into a U, so that the conductor element and the sensor element are fixed by the contact holder and put into conductive contact. The other leg of the conductor element is disposed in one of the through holes. A spring element for nonpositive connection of the conductor element to the contact face of the sensor element is not provided in this clamp contacting means.

SUMMARY OF THE INVENTION

The gas probe of the invention has the advantage over the prior art that deformation of the conductor element from creeping processes can be largely prevented, even at high temperatures, for instance in the range of 800° C., so that impairment of the contacting of the sensor element is precluded.

Because the conductor element is disposed in an indentation in the contact holder and is in contact with the contact face only by a region that protrudes from the indentation in the contact holder, it is attained that deformation of at least the part of the conductor element located in the indentation in the contact holder is reduced or even prevented entirely. Thus the contact pressure exerted by the spring element is at least largely maintained even at high temperatures, and thus adequate contact of the conductor element and contact face of the sensor element is assured.

Creeping is averted especially reliably if the conductor element protrudes by less than half its cross-sectional area from the indentation in the contact holder. Because the majority of the conductor element is located in the indentation, only the smaller part, protruding out of the indentation, of the conductor element can be subject to deformation, thus minimizing the loss of contact pressure from creeping of the conductor element.

Because the part of the conductor element located in the indentation makes up more than half the indentation in cross section, it is attained that the loss of initial tension from the deformation of the conductor element in the indentation that occurs in operation at high temperatures is only slight. The loss in initial tension is moreover calculable, since at most the conductor element can creep only until the indentation is entirely filled. Thus the loss of initial tension can be compensated for by the provision of a spring element, which has a correspondingly higher initial tension before the deformation of the conductor element occurs in the indentation.

If the conductor element is disposed by positive engagement in the indentation, deformation of the conductor element in the indentation is prevented entirely.

Because a high-temperature-resistant material is provided for the conductor element, the tendency to deformation at high temperatures is reduced.

BRIEF DESCRIPTION OF THE DRAWINGS

The invention will be described in detail herein below in conjunction with the drawings, in which.

DESCRIPTION OF THE PREFERRED EMBODIMENT

Figure 1:
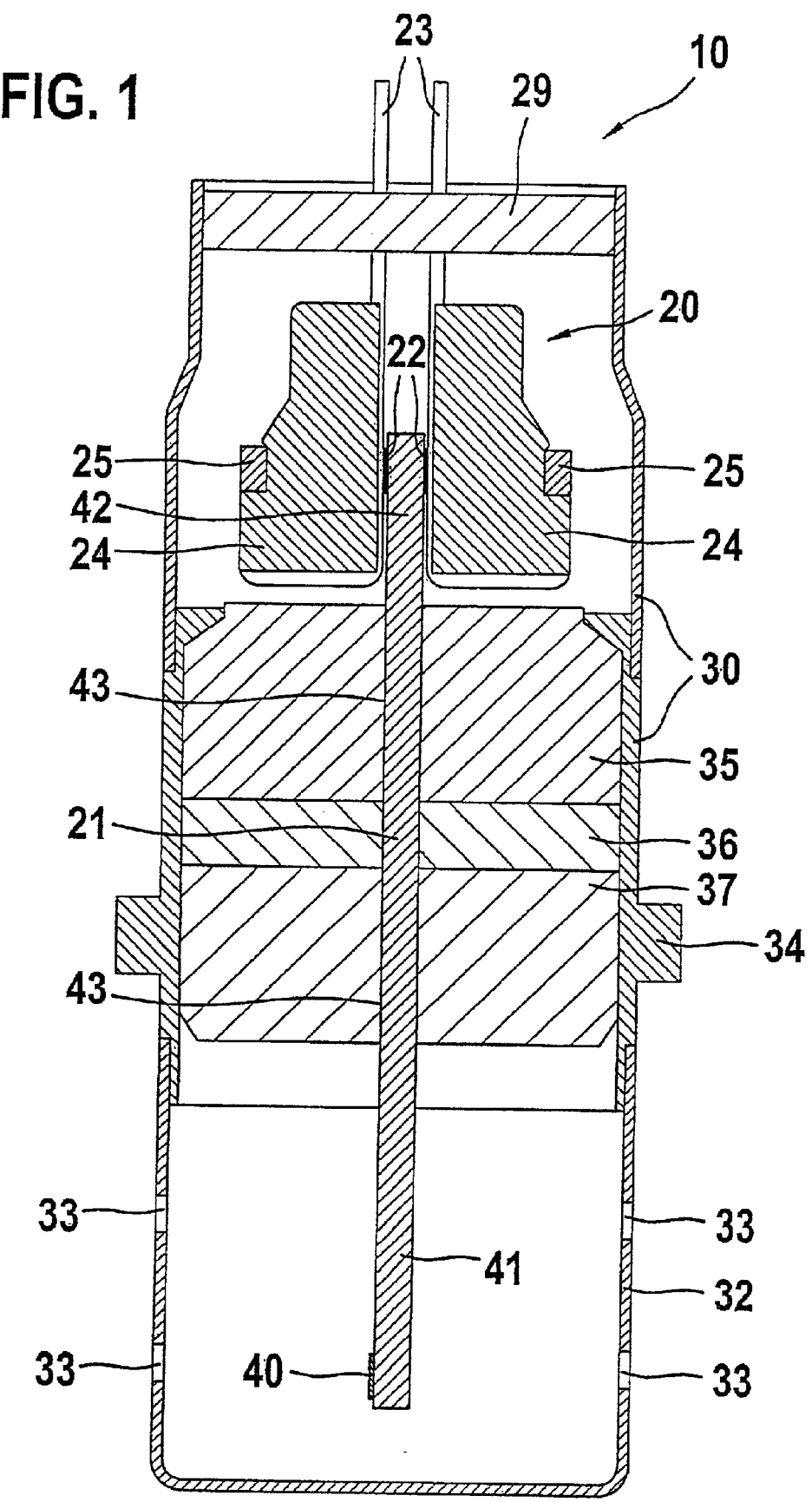
FIG. 1 shows a cross section through one embodiment of a gas probe of the invention with a contacting device.

FIG. 1 shows a gas probe 10 with a metal housing 30, in which two ceramic molded parts 35, 37, one on the connection side and one on the measurement gas side, are disposed. The two ceramic molded parts 35, 37 each have an opening 43, the openings extending in alignment with one another, in which a chip-shaped sensor element 21 is located with one end portion 41 on the measurement gas side and another end portion 42 on the connection side. Between the ceramic molded parts 35, 37 on the connection and measurement gas sides, there is a sealing element 36.

The end portion 41 of the sensor element 21 on the measurement gas side protrudes out of the housing 30 and is surrounded by a protective tube 32, which is fixed to the housing 30. The gas probe 10 is secured by means of a collar 34 in a measurement opening, not shown, of a measurement gas chamber, such as an exhaust gas line of an internal combustion engine. The gas to be measured passes through inlet and outlet openings 33 of the protective tube 32 to reach a measurement point 40 located on the end portion 41 on the measurement gas side of the sensor element 21.

The end portion 42 toward the connection side of the sensor element 21 has contact faces 22, for which a contacting device 20 with conductor elements 23, contact holders 24 and one spring element 25 is provided. The conductor elements 23 lead out of the housing 30 into a connection line, not shown, which is connected to evaluation electronics, also not shown. On the connection side, the housing 30 is closed off by a disk 29 which has openings for the conductor elements 23.

Figure 2:
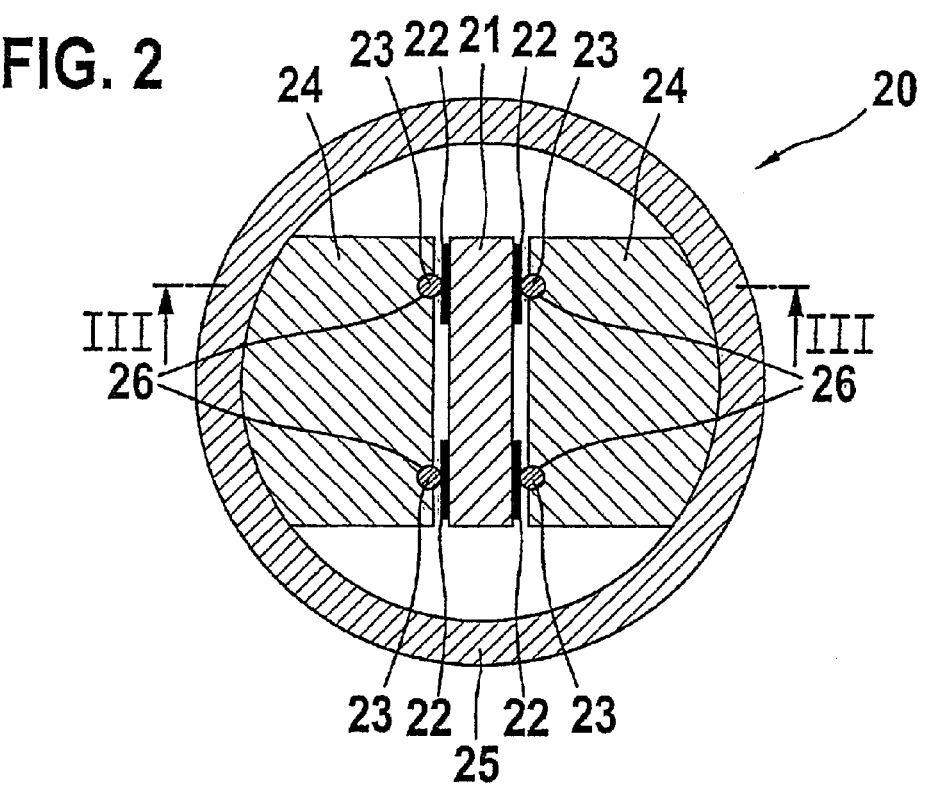
FIG. 2 shows a sectional view of the contacting device taken along the line II—II of FIG. 3.
Figure 3:
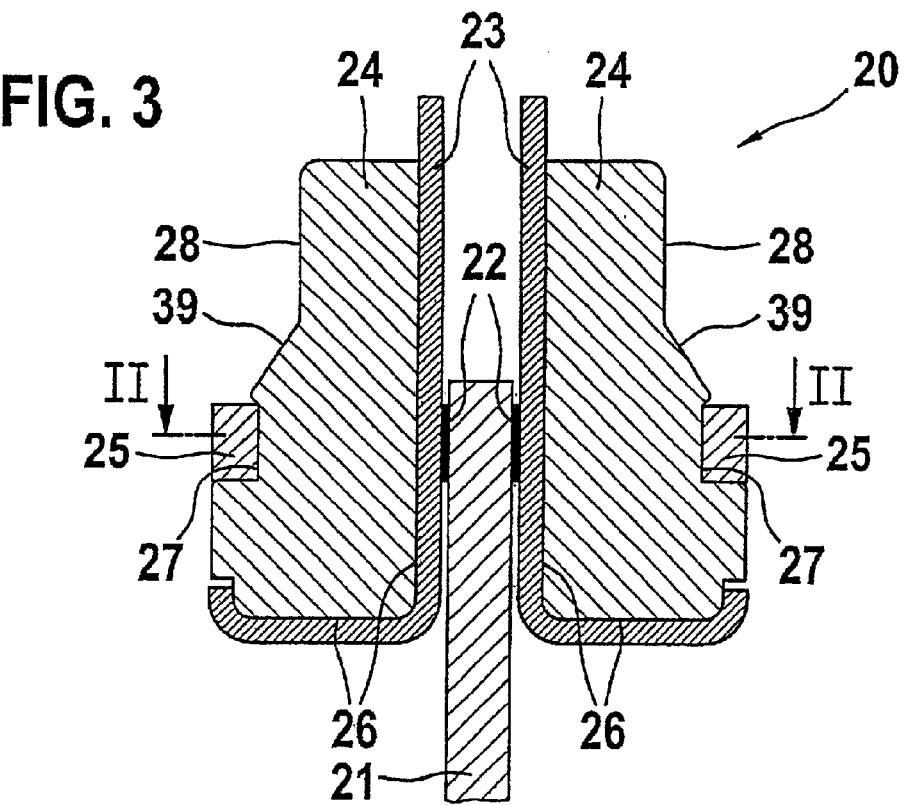
FIG. 3 shows a sectional view of the contacting device taken along the line III—III of FIG. 2.

FIGS. 2 and 3 show an enlarged view of the region of the contacting device 20 of the embodiment of the invention shown in FIG. 1. The end portion 42 on the connection side of the sensor element 21 has four contact faces 22, of which two each are disposed on the two outer large faces of the sensor element 21. The two contact holders 24 of the contacting device 20 each have two indentations 26, on the side toward the sensor element 21, in which indentations the conductor elements 23 are disposed by positive engagement. With the part protruding from the indentations 26, the conductor elements 23 are in contact with the respective contact faces 22 of the sensor element 21. The conductor elements 23 are pressed onto the contact faces 22 by the spring element 25 that engages the contact holders 24.

The indentations 26 of the contact holder 24 are provided not only on the side toward the contact faces 22 of the sensor element 21; they also surround the contact holder 24 on the side toward the measurement gas chamber and are also located at least in some regions on the side remote from the contact faces 22 of the sensor element 21. The conductor elements 23 extend within the indentations 26 and are fixed to the contact holder 24 by means of their appropriate hooklike shape.

The spring element 25 rests in a detent shoulder 27 of the two contact holders 24 and via the contact holders 24 presses the conductor elements 23 onto the respective contact faces 22 of the sensor element 21. The detent shoulder 27 is disposed at the level of the contact faces 22; that is, the contact faces 22 are located at least in some regions in the interior of the annular spring element 25 that is located in the detent shoulder 27. The contact holders 24 have a further detent shoulder 28, in which the spring element 25 rests without initial tension and outward from which the spring element 25 can be slipped a chamfer 39 onto the detent shoulder 27.

The contact holders 24 comprise a ceramic material, preferably $Al_2O_3$. The conductor elements 23 comprise a high-temperature-resistant material, preferably nickel (99.6%) or $NiCr_2MnSi$ (2.4146).

In the present exemplary embodiment, the conductor elements 23 have a round cross-sectional area, are introduced by positive engagement into the indentations 26 of the contact holders 24, and protrude with approximately one-third of their cross-sectional area from the indentations 26. Other embodiments of the invention are also conceivable, in which the conductor elements have rectangular or oval cross-sectional areas, for instance. It is also conceivable for the conductor elements upon assembly not to rest by positive engagement in the indentations of the contact faces. In that case, it should be assured by the choice of cross-sectional areas of the conductor element and of the indentation that the conductor element, at the high temperatures that occur during operation, will deform only to such an extent that the part of the conductor element protruding from the indentation descends only slightly into the indentation as a result of the deformation, so that the loss of initial tension thus remains slight.

In the present exemplary embodiment, the sensor element 21 has four contact faces 22. A sensor element of this kind is used for instance in gas probes that serve to measure the concentration of an exhaust gas component, such as oxygen, in exhaust gases of internal combustion engines. For one skilled in the art it is readily possible to adopt the invention in other gas sensors whose sensor elements have more or fewer than four contact faces. For instance, temperature probes that operate by the method of resistance measurement often have two contact faces. If the contact faces are disposed on opposite outer faces of the sensor element, then one indentation, disposed for instance in the middle, in each contact holder suffices to receive one conductor element. If all the contact faces are disposed on the same outside face of the sensor element, then the conductor elements on the side opposite the contact faces can be omitted, so that on that side the contact holder rests directly on the sensor element. It is also conceivable to retain the design of the present exemplary embodiment and for the conductor elements not to be contacted to the evaluation electronics on the side of the sensor element opposite the contact faces.

The foregoing relates to preferred exemplary embodiments of the invention, it being understood that other variants and embodiment thereof are possible within the spirit and scope of the invention, the latter being defined by the appended claims.

What is claimed is:

1. A gas probe for installation in an exhaust gas line of an internal combustion engine for determining at least one property of a gas in the exhaust line, the gas probe comprising a metal housing, an essentially planar sensor element (21) disposed in the metal housing in electrically insulated fashion, the sensor element having at least one contact face (22) which is conductively connected to a metal conductor element (23), and an electrically insulating contact holder (24) for the conductor element (23), a contact spring (25) pressing the conductor element (23) against the contact face (22), the spring element (25) engaging the contact holder (24), the contact holder (24) including an indentation (26) with the conductor element (23) disposed in the indentation (26) of the contact holder (24), the indentation being oriented toward the contact face (22) of the sensor element (21), a region of the conductor element (23) protruding from the indentation (26) of the contact holder (24) and being in contact with the contact face (22) under the influence of the spring element (25).

2. The gas probe of claim 1, wherein the conductor element (23) protrudes with less than half its contact face from the indentation (26) of the contact holder (24).

3. The gas probe of claim 1, wherein the region of the conductor element (23) located in the indentation (26) in its cross section fills more than half of the indentation (26).

4. The gas probe of claim 1, wherein the conductor element (23) in at least some regions is located by positive engagement in the indentation (26) of the contact holder (24).

5. The gas probe of claim 1, wherein the spring element (25) is an elastic, hollow-cylindrical element.

6. The gas probe of claim 1, wherein the conductor element (23) has a high-temperature-resistant material.

7. The gas probe of claim 1, wherein the conductor element (23) is a wire, which contains nickel (99.6%) or $NiCr_2MnSi$ (2.4146).

8. The gas probe of claim 1, wherein the contact holder (24) contains $Al_2O_3$.

9. The gas probe of claim 1, wherein contact holder (24) comprises a detent shoulder (27), onto which the spring element (25) can be slipped via a chamfer (39), the spring element (25) being located in the detent shoulder (27) and pressing the conductor element (23), by means of the spring force of the spring element, onto the contact face (22) of the sensor element (21).

10. The gas probe of claim 9, wherein the contact holder (24) comprises a further detent shoulder (28), in which the spring element (25) can rest without initial stress.

11. The gas probe of claim 1, wherein the contact holder (24) comprises a further detent shoulder (28), in which the spring element (25) can rest without initial stress.

* * * * *